US00PP15300P3

(12) United States Plant Patent
Challet

(10) Patent No.: US PP15,300 P2
(45) Date of Patent: Nov. 9, 2004

(54) ***CHRYSANTHEMUM* PLANT NAMED 'CHASIX'**

(50) Latin Name: *Ajania pacifica*
Varietal Denomination: Chasix

(75) Inventor: Jean-Pierre Challet, Nuaillé (FR)

(73) Assignee: Selection New Plant Sarl, Le Luc en Provence (FR)

( * ) Notice: Subject to any disclaimer, the term of this patent is extended or adjusted under 35 U.S.C. 154(b) by 33 days.

(21) Appl. No.: 10/342,259

(22) Filed: Jan. 15, 2003

(65) Prior Publication Data

US 2004/0139513 P1 Jul. 15, 2004

(51) Int. Cl.[7] ..... A01H 5/00
(52) U.S. Cl. ..... Plt./263
(58) Field of Search ..... Plt./263, 284

*Primary Examiner*—Anne Marie Grunberg
(74) *Attorney, Agent, or Firm*—Burns, Doane, Swecker & Mathis, L.L.P.

(57) ABSTRACT

A new and distinct Charm *Chrysanthemum* cultivar is provided that is the result of a controlled breeding program. Attractive small daisy-like blossoms are formed in profusion in clusters having yellow-green disc florets and one row of white ray florets. The growth habit is short, bushy, very compact and well-branched with short internodes and yields a generally uniform and spherical overall plant. The foliage is small and dark green, and blends well with the yellow-green and white blossom coloration. The upper surface of the leaves possesses a margin that is light greyed-green in coloration. The response time is approximately eight weeks. The natural flowering time is late-October. When mature the blossoms emit yellow pollen. The plant grows well in pots, and possesses no particular susceptibility to disease and pests.

1 Drawing Sheet

Figure 1:
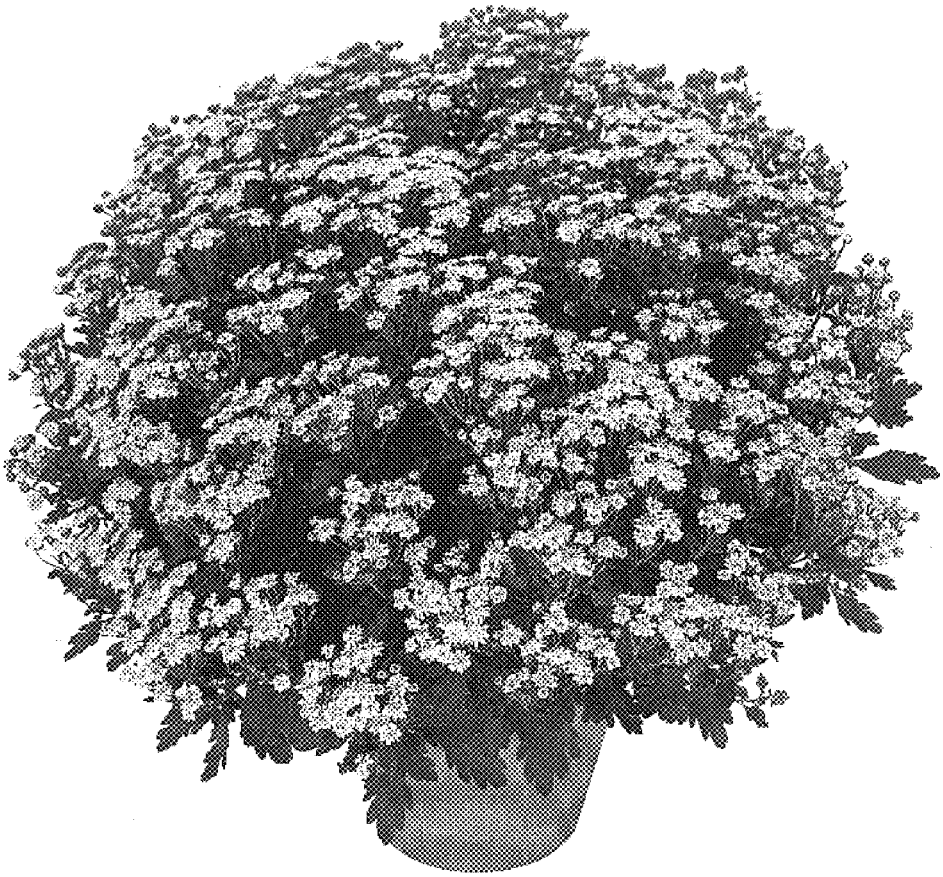

Botanical/commercial classification: *Ajania pacifica*/ Decorative Pot Mum.
Varietal denomination: cv. 'Chasix'.

SUMMARY OF THE INVENTION

The present invention comprises a new and distinct cultivar of *Chrysanthemum,* botanically known as *Ajania pacifica*, and hereafter is referred to by the cultivar name 'Chasix'.

The new cultivar of the present invention was created at Nuaillé, France during the course of a controlled breeding program. The seed parent (i.e., the female parent) was an unnamed plant of the species, and the pollen parent (i.e., the male parent) was designated '92/27/3'. Neither parent was patented in the United States. The seeds resulting from the cross were sown and small plants were obtained which were physically and biologically different from each other. Selective study resulted in the identification of a single plant of the new cultivar of the present invention.

It was found that the new Charm *Chrysanthemum* cultivar of the present invention displays:

(a) a short, bushy, compact, well-branched, and generally spherical growth habit with short internodes, (b) profusely forms attractive small daisy-like blossoms having yellow-green disc florets and one row of white ray florets, (c) forms decorative small dark green foliage with a light greyed-green margin on the upper leaf surface, (d) forms yellow pollen when the blossoms are mature, and (e) an ability to grow well in pots.

The new cultivar can be grown singly or in clumps in pots. It also can be grown in the landscape. The yellow-green and white blossoms blend nicely with the gray-green foliage. The plant is self-branching and the internodes are short. Pinching is helpful to further enhance branching and produces a large number of shoots; however, such pinching is not necessary since the plant already is inherently well branched. The natural flowering time is late-October.

The new cultivar can be readily distinguished from its parental plants. More specifically, the female parent displays whitish-yellow ray florets, a less busy growth habit, and is natural flowering approximately three weeks later than the new cultivar. The '92/27/3' male parent forms dissimilar larger flowers with more petals that are slightly squared and serrated, and more typical foliage that lacks a light greyed-green margin on the upper surface that is possessed by the new cultivar. No other closely related cultivar is known to Applicant.

Asexual reproduction of the new cultivar by the use of cuttings as performed at Nuaillé, France, in a controlled environment has demonstrated that the characteristics of the new cultivar are firmly fixed and are retained through successive generations of asexual propagation.

'Chasix' has not been observed under all possible environmental conditions to date. Accordingly, it is possible that the phenotype may vary somewhat with variations in the environment, such as temperature, light, day length, contact with pesticides and/or subjection to grown regulation treatments.

BRIEF DESCRIPTION OF THE PHOTOGRAPH

The accompanying FIG. 1 depicts a typical eighteen week-old plant of 'Chasix' cultivar while growing in a pot in a greenhouse at Nuaillé, France. The attractive compact spherical growth habit, with a substantially homogenous coverage of yellow-green and white blossoms, and dark green foliage with a light greyed-green margin on the upper leaf surface are illustrated.

DETAILED DESCRIPTION

The plants described were grown in pots in a greenhouse at Nuaillé, France. No growth regulation was used. The growing conditions approximate those commonly utilized for the commercial production of decorative pot mums.

General appearance: Short, bushy, and compact with a generally spherical growth habit. The internodes are short and commonly measure approximately 10 to 25 mm on average. When a cutting is placed during week 23 in a four-liter pot, the resulting plant commonly will display a height of approximately 28 to 30 cm on average and a width of approximately 45 to 50 cm on average at the end of flowering during late October.

Foliage: The leaves are approximately 5 to 7 cm in length on average. Each leaf possesses rough serration and consists of five lobes. The lobes generally possess murcronate tips, the inferior lobe is medium in size, and the sinus between lobes generally is rounded. The upper leaf surface is dark green (near Green Group 139A) and bears a light-colored margin of Greyed-Green Group 191A. The under leaf surface also is near Greyed-Green Group 191A in coloration. The nervure coloration is near Green Group 139A on the upper surface and near Greyed-Green Group 191A on the under surface. The stems are near Greyed-Green Group 195A in coloration, and the petioles are near Greyed-Green Group 191A in coloration.

Flowers: The attractive small daisy-like blossoms are formed in clusters. The buds possess a smooth surface texture, commonly are approximately 0.5 to 0.7 cm in length on average, and near Green Group 137D in coloration. The flower coverage is substantially homogeneous across the plant. Accordingly, the flowers are so closely grouped as to substantially cover the circumference of the dome-shaped plant. The flower emits a very slight fragrance similar to that of honey. The disc florets are yellow-green and are surrounded by one row of white (slightly whiter than White Group 155C) ray florets when mature. The number of petals per flower commonly approaches 20 and the petals commonly measure approximately 0.4 to 0.6 cm on average. The flower diameter when mature commonly ranges from approximately 10 to 15 mm. The stigma is near Yellow Group 2A in coloration. The styles, filaments and anthers are so small and slim that it is not possible to determine their coloration and to provide additional characterization using standard evaluation techniques. Yellow pollen commonly is displayed in the mature blossoms that is near Yellow Group 2A in coloration.

Flower time: The natural flowering time is late-October. The flowers commonly last approximately 6 to 8 days on average on the plant and such longevity commonly is influenced by the environmental conditions that are encountered.

Response time: The time between the beginning of the short day period and the flowering date at normal temperature and light intensity is approximately eight weeks.

Usage: Decorative pot mum. No particular susceptibility to diseases and pests has been observed during the growing of the new cultivar to date.

I claim:

1. A new and distinct cultivar of Charm *Chrysanthemum* plant that displays:

(a) a short, bushy, compact, well-branched, and generally spherical growth habit with short internodes, (b) profusely forms attractive small daisy-like blossoms having yellow-green disc florets and one row of white ray florets, (c) forms decorative small dark green leaves with a light greyed-green margin on the upper leaf surface, (d) forms yellow pollen when the blossoms are mature, and (e) an ability to grow well in pots;

substantially as illustrated and described.

* * * * *